United States Patent [19]
Pillai

[11] Patent Number: 6,050,965
[45] Date of Patent: Apr. 18, 2000

[54] CERVICAL COLLAR FOR LIFTING THE SKULL OF A WEARER

[76] Inventor: Bala Hari Pillai, 912 Roanoke Ave., Riverhead, N.Y. 11901

[21] Appl. No.: 09/177,579

[22] Filed: Oct. 23, 1998

[51] Int. Cl.[7] ........................................... A61F 5/00
[52] U.S. Cl. .................... 602/18; 602/13; 128/DIG. 23
[58] Field of Search ................... 602/13, 17, 18; 128/845, 846, DIG. 23

[56] References Cited

U.S. PATENT DOCUMENTS

| | | | |
|---|---|---|---|
| 3,285,244 | 11/1966 | Cottrell | 602/18 |
| 3,343,532 | 9/1967 | Zumaglini | 602/18 |
| 4,205,667 | 6/1980 | Gaylord | 602/18 |
| 5,752,927 | 5/1998 | Rogachevsky | 602/18 |

*Primary Examiner*—Michael A. Brown

[57] ABSTRACT

A cervical collar for lifting the skull of a wearer. The collar includes a core, a pair of bladders, and inflating apparatus. The core replaceably encircles the neck of the wearer. The pair of bladders are inflatable and disposed on the core. The inflating apparatus is in fluid communication with the pair of bladders, and when the pair of bladders are inflated to a predetermined pressure by the inflating apparatus, the skull of the wearer is gently pushed off the shoulders of the wearer, which relieves downward pressure on the cervical spine of the wearer by forming intrinsic neck traction, whose early and continued use relieves pain and weakness and prevents major and sometimes non-reversible deterioration of the cervical spine of the wearer.

7 Claims, 5 Drawing Sheets

CERVICAL COLLAR FOR LIFTING THE SKULL OF A WEARER

BACKGROUND OF THE INVENTION

1. Field of the Invention

The present invention relates to a cervical collar. More particularly, the present invention relates to a cervical collar for lifting the skull of a wearer.

2. Description of the Prior Art

One of the most common afflictions of mankind is pain in the neck. This is in most instances due to the fact that human beings were not really designed to walk upright.

In the evolutionary process, humanoids began to walk upright from being on all four limbs earlier on. In the position where an animal is on all four limbs, the weight of the head is essentially pulled downwards, by the force of gravity.

In developing the ability to walk upright, the weight of the head (in the adult from 8 to 10 lbs.), was now born by the cervical spine. This area of the spinal column is the weakest part of the entire human body and is liable to all forms of injury, both acute and chronic. Structurally, the skeleton here consists of eight vertebral segments out of a total of thirty four for the entire vertebral column.

Between the bony vertebrae are "discs" made of cartilage and serve as cushions and "shock absorbers." On either side of the bony vertebrae are supporting structures that include ligaments and muscles. Through openings in the bony vertebrae, called foraminae, nerves from the spinal cord, which is the extension down from the brain, exit to supply various parts of the body. In the cervical spine, this mainly consists of the supply to the upper extremities. These nerves are responsible for the sensory (for example the feeling of pain and temperature) and motor activity for the arms (for example movement of the wrist or the ability to grip objects).

The anatomy of the neck is such that the head is allowed to move up and down, left and right, diagonally either way, or a combination of these movements. This degree of flexibility of the neck, however, comes at a price.

There is in many humans, early deterioration of the discs leading to pain in the neck. This pain is in most instances due to the tightening or spasm of the muscles around the spine at this area. In more serious cases, the deterioration is so severe that there is no cushioning effect of the discs left, and there will be actual rubbing of bone upon bone in certain positions of the head.

When the nerves supplying a particular segment of the body is impinged by the deteriorating vertebral bodies or pressed upon by the formation of osteophytes, which are pieces of new bone growth as a result of injury or inflammation, there will be pain radiating to that part of the body that is called radiculopathy.

In severe cases of radiculopathy, the nerves supplying muscles may be affected causing weakness and possibly paralysis of the affected muscles. An example of such a problem would be when there is radiculopathy of the cervical segment nerves 6 to 8 (C6, C7, and C8). These nerve segments supply the entire upper extremities from the shoulders to the fingers. When the nerves concerned with sensation are involved, there will be pain in the hand of the affected side and when the nerves that supply the muscles are affected, there may be weakness in the hand and possibly paralysis, which in turn leads to a poor or absent grip.

One of the factors that has caused the widespread prevalence of this form of cervical spine disc deterioration is the use of automobiles, as driving is very bad for the neck in general. A more recent occupational hazard as a casual effect, is the increasing use of computers in this society. In both instances, there is increased physical stress on the discs due to constant positioning needs of the head for proper vision leading in turn to premature wearing out.

Presently, the treatment of mild to moderate forms of cervical disc deterioration consists of wearing a cervical support collar and physical therapy, in addition to relief measures for pain that could include medication. This form of therapy consists mainly of neck stretching exercises, application of heat, and in selected cases, the use of "neck traction."

This form of neck traction, called external or extrinsic, is a cumbersome procedure that actually lifts the head off the cervical spine. Though this is effective in most cases, it can be done only intermittently, for short periods of time, and needs professional supervision throughout. Thus, there exists a pressing need for traction that is effective, easy to use, safe, easy to manufacture, inexpensive, and does not require professional supervision.

SUMMARY OF THE INVENTION

ACCORDINGLY, AN OBJECT of the present invention is to provide a cervical collar for lifting the skull of a wearer that avoids the disadvantages of the prior art.

ANOTHER OBJECT of the present invention is to provide a cervical collar for lifting the skull of a wearer that is simple and inexpensive to manufacture.

STILL ANOTHER OBJECT of the present invention is to provide a cervical collar for lifting the skull of a wearer that is simple to use.

BRIEFLY STATED, YET ANOTHER OBJECT of the present invention is to provide a cervical collar for lifting the skull of a wearer. The collar includes a core, a pair of bladders, and inflating apparatus. The core replaceably encircles the neck of the wearer. The pair of bladders are inflatable and disposed on the core. The inflating apparatus is in fluid communication with the pair of bladders, and when the pair of bladders are inflated to a predetermined pressure by the inflating apparatus, the skull of the wearer is gently pushed off the shoulders of the wearer, which relieves downward pressure on the cervical spine of the wearer by forming intrinsic neck traction, whose early and continue use relieves pain and weakness and prevents major and sometimes non-reversible deterioration of the cervical spine of the wearer.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures of the drawing are briefly described as follows.

Figure 1:
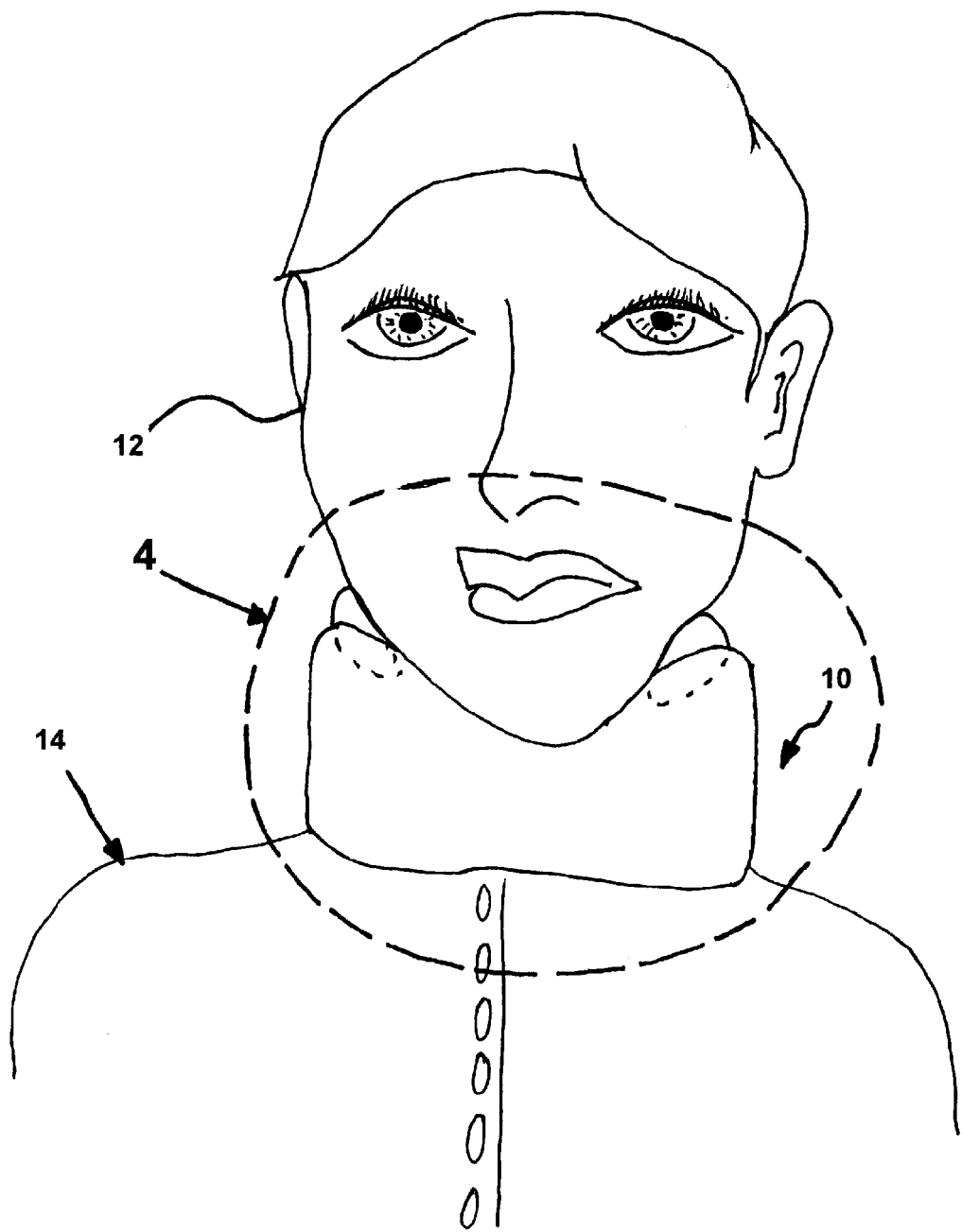
FIG. 1 is a diagrammatic front perspective view of the present invention in use.

LIST OF REFERENCE NUMERALS UTILIZED IN THE DRAWING 10 cervical collar for lifting the skull of a wearer of the present invention
12 skull of wearer 14
14 wearer
16 core for replaceably encircling neck 17 of wearer 14
17 neck of wearer 14
18 pair of bladders
20 inflating apparatus
22 shoulders of wearer 14
24 cervical spine of wearer 14
25 jaw of wearer 14
26 pair of ends of core 16 for facing back 28 of neck 17 of wearer 14 when core 16 is in wearing position
28 back of neck 17 of wearer 14
30 mating portions of hook and loop fasteners
32 adjoining faces of pair of free ends 26 of core 16
34 inner surface of core 16
36 pair of sides of inner surface 34 of core 16 for facing sides 37 of neck 17 of wearer 14
37 sides of neck 17 of wearer 14
38 upper edge of each bladder of pair of bladders 18 for facing skull 12 of wearer 14
40 proximal end of upper edge 38 of each bladder of pair of bladders 18
42 cushion for contacting point behind respective angle of jaw 25 of wearer 14
44 distal end of upper edge 38 of each bladder of pair of bladders 18
46 another cushion for contacting base 48 of skull 12 of wearer 14, at respective nuchal point on respective side of base 48 of skull 12 of wearer 14
48 base of skull 12 of wearer 14
50 tube
52 filler tube of inflating apparatus 20
54 one end of filler tube 52 of inflating apparatus 20
56 another end of filler tube 52 of inflating apparatus 20
58 squeezable hand bulb of inflating apparatus 20
60 set of relief valves of inflating apparatus 20
62 cover

DETAILED DESCRIPTION OF THE PREFERRED EMBODIMENT

Figure 2:
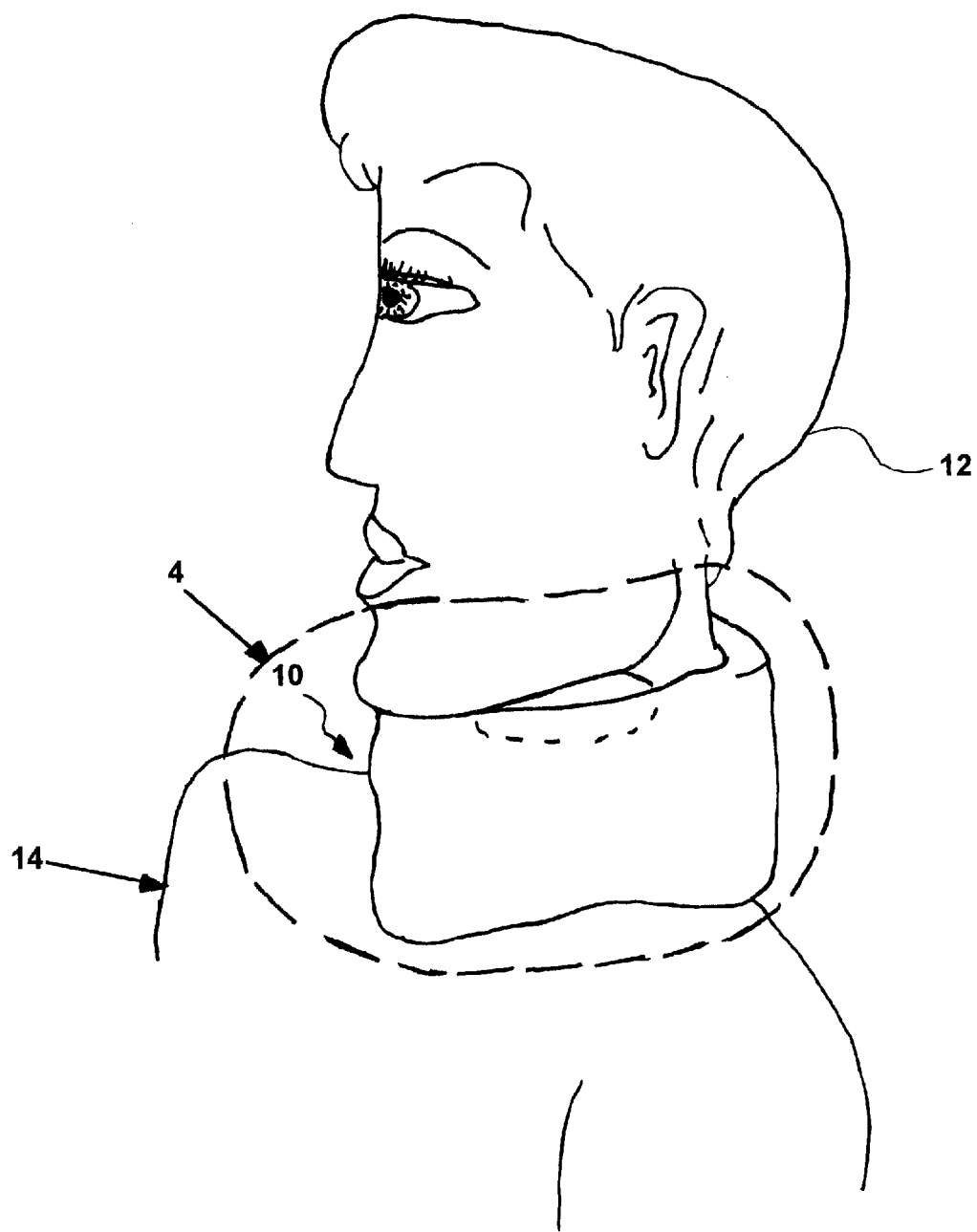
FIG. 2 is a diagrammatic side perspective view of the present invention in use.
Figure 3:
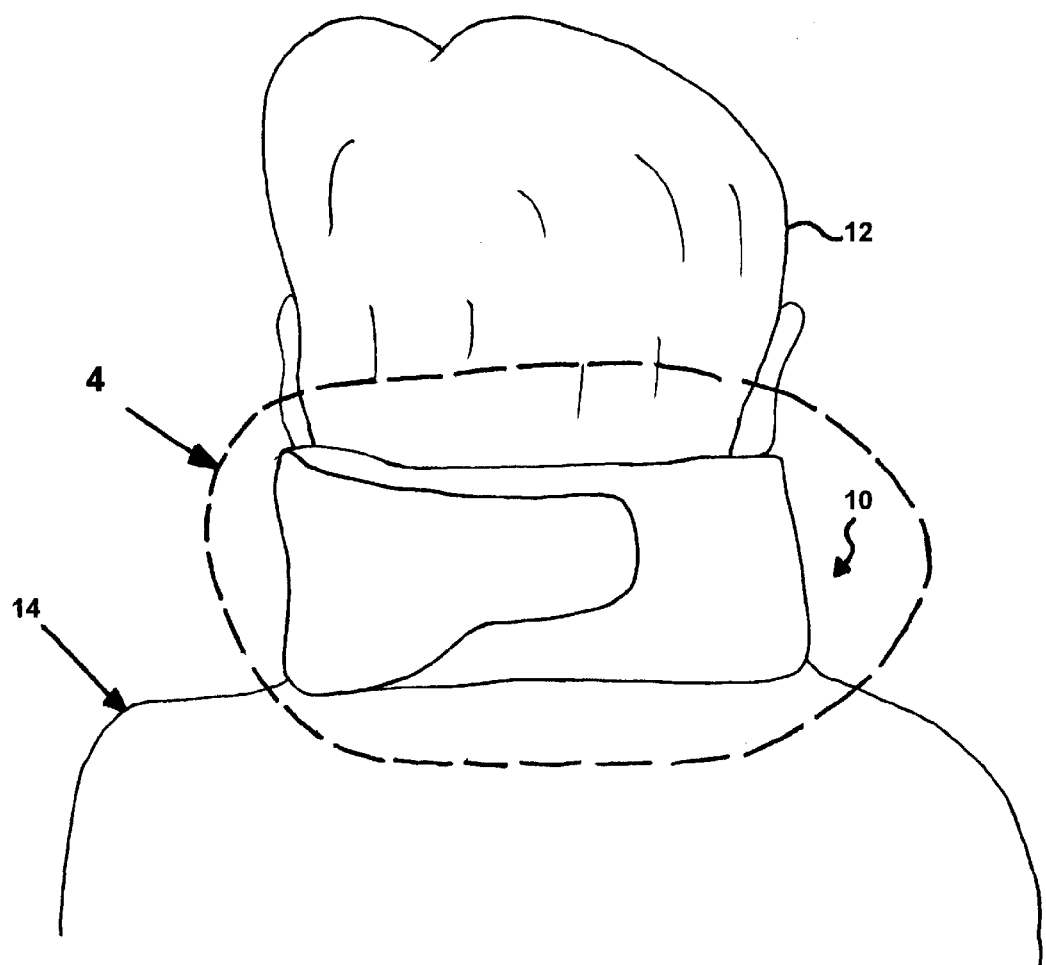
FIG. 3 is a diagrammatic rear perspective view of the present invention in use.

Referring now to the figures, in which like numerals indicate like parts, and particularly to FIGS. 1–3, which are, respectively, a diagrammatic front perspective view of the present invention in use, a diagrammatic side perspective view of the present invention in use, and a diagrammatic rear perspective view of the present invention in use, the cervical collar for lifting the skull of a wearer of the present invention is shown generally 10 for lifting the skull 12 of a wearer 14.

Figure 4:
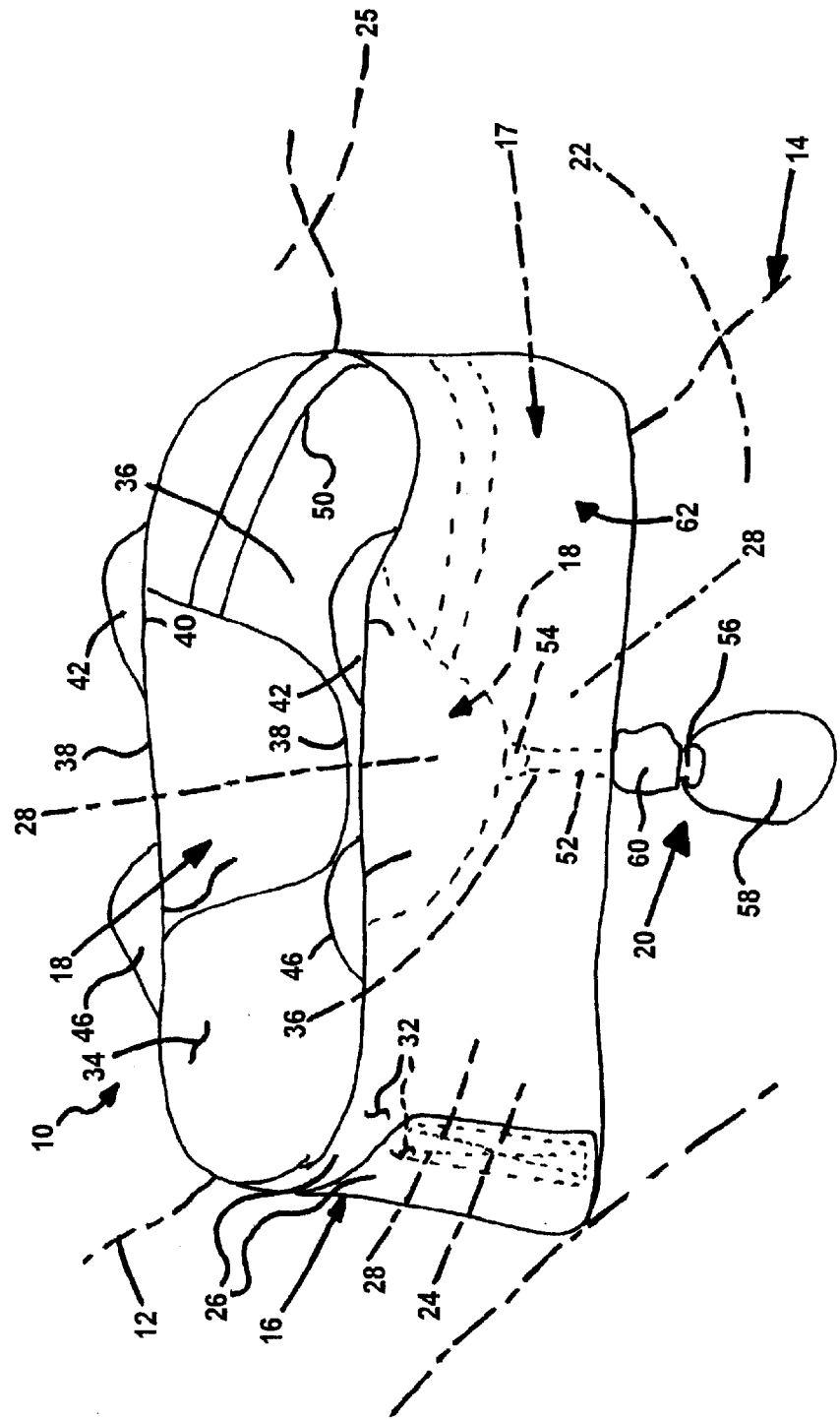
FIG. 4 is an enlarged diagrammatic perspective view of the area generally enclosed by the dotted ellipses identified by ARROWS 4 in FIGS. 1–3 of the present invention in the closed position.
Figure 5:
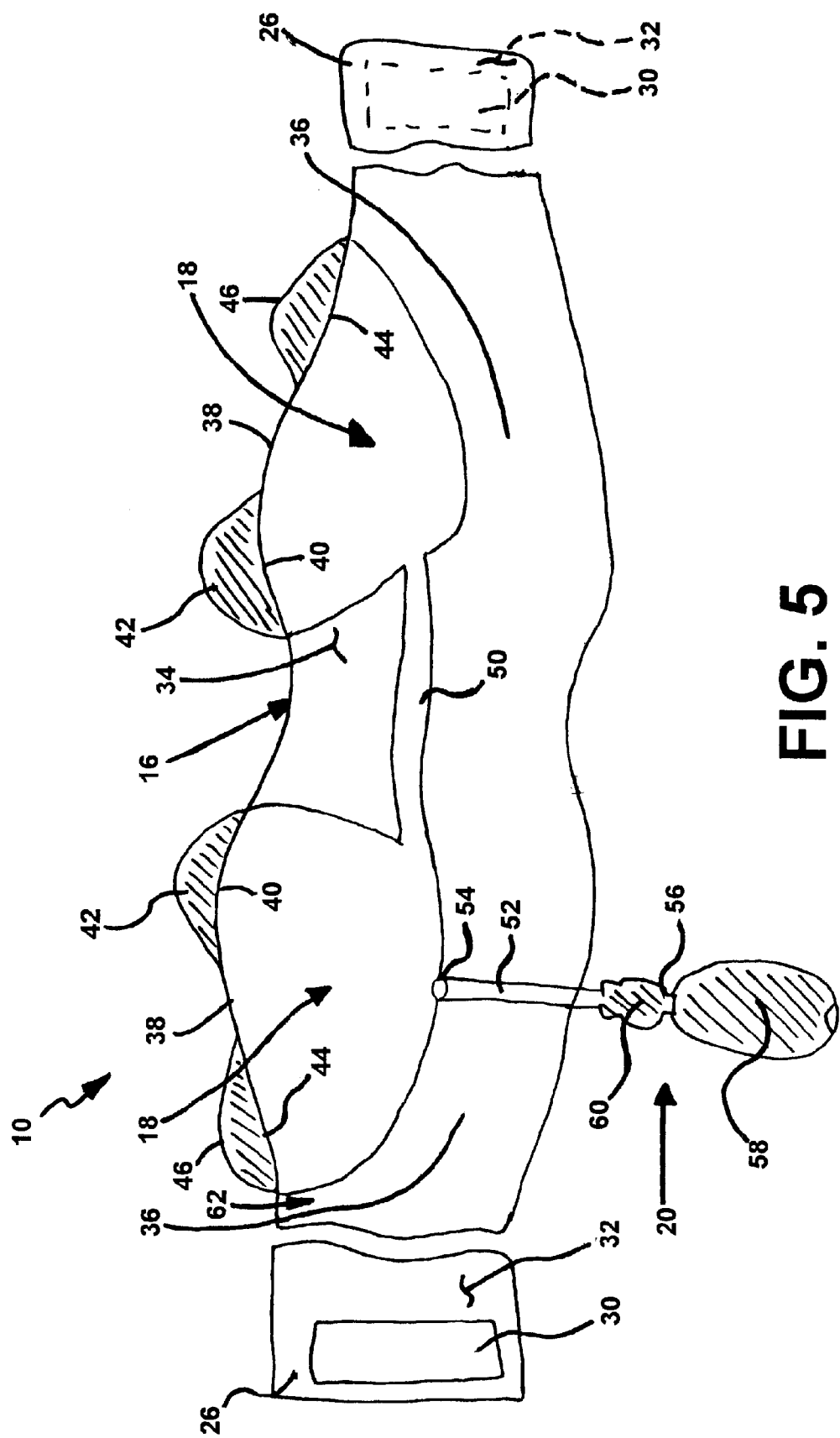
FIG. 5 is a diagrammatic perspective view of the present invention shown in FIG. 4 in the open position.

The configuration of the cervical collar for lifting the skull of the wearer 10 can best be seen in FIGS. 4–5, which are, respectively, an enlarged diagrammatic perspective view of the area generally enclosed by the dotted ellipses identified by ARROWS 4 in FIGS. 1–3 of the present invention in the closed position, and a diagrammatic perspective view of the present invention shown in FIG. 4 in the open position, and as such, will be discussed with reference thereto.

The cervical collar for lifting the skull of a wearer 10 comprises a core 16 for replaceably encircling the neck 17 of the wearer 14 and has a non-wearing position and a wearing position, a pair of bladders 18 being inflatable and disposed on the core 16, and inflating apparatus 20 in fluid communication with the pair of bladders 18, and when the pair of bladders 18 are inflated to a predetermined pressure by the inflating apparatus 20, the skull 12 of the wearer 14 is gently pushed off the shoulders 22 of the wearer 14 which relieves downward pressure on the cervical spine 24 of the wearer 14 by forming intrinsic neck traction whose early and continued use relieves pain and weakness and prevents major and sometimes non-reversible deterioration of the cervical spine 24 of the wearer 14.

The core 16 generally resembles presently available support collars and is washable foam and has a consistency in a range of soft to firm, depending upon needs of the wearer 14.

The pair of bladders 18 are manufactured from washable latex and flexible enough to allow for movement of the neck 17 of the wearer 14 in all directions, while allowing for movement of the jaw 25 of the wearer 14 for talking and eating without sacrificing any upwardly lifting pressure of the pair of bladders 18.

The core 16 has a pair of free ends 26 that overlap for facing the back 28 of the neck 17 of the wearer 14 when the core 16 is in the wearing position, with the core 16 being releasably maintained in the wearing position by mating portions of hook and loop fasteners 30 that are disposed on adjoining faces 32 of the pair of free ends 26 of the core 16.

The core 16 further has an inner surface 34 with a pair of sides 36 for facing the sides 37 of the neck 17 of the wearer 14, with each bladder of the pair of bladders 18 being disposed on a respective side of the pair of sides 36 of the inner surface 34 of the core 16.

Each bladder of the pair of bladders 18 has an upper edge 38 for facing the skull 12 of the wearer 14. The upper edge 38 of each bladder of the pair of bladders 18 has a proximal end 40 with a cushion 42 thereon for contacting a point behind a respective angle of the jaw 25 of the wearer 14 and a distal end 44 with another cushion 46 thereon for contacting the base 48 of the skull 12 of the wearer 14, at a respective nuchal point on a respective side of the base 48 of the skull 12 of the wearer 14, with the point behind the respective angle of the jaw 25 of the wearer 14 and the respective nuchal point on the respective side of the base 48 of the skull 12 of the wearer 14 being those portions of the skull 12 of the wearer 14 that are sufficient for handling upward supporting and lifting pressure when the pair of bladders 18 are inflated.

The pair of bladders 18 are in fluid communication with each other by a tube 50 that extends along the inner surface 34 of the collar 16, opposite to the pair of free ends 26 of the core 16.

The inflating apparatus 20 comprises a filler tube 52 that depends at one end 54 thereof from, and in fluid communication with, one bladder of the pair of bladders 18, and terminates at another end 56 thereof.

The inflating apparatus 20 further comprises a squeezable hand bulb 58 that is in fluid communication with the another end 56 of the filler tube 52 of the inflating apparatus 20, and which is similar to those used in syphgmomanometers and blood pressure monitoring devices, and when squeezed, inflates the pair of bladders 18.

The squeezable hand bulb 58 of the inflating apparatus 20 is interchangeably disposed on the another end 56 of the filler tube 52 of the inflating apparatus 20 so as to be useable with successive cervical collars for lifting the skull of a wearer 10 which makes the squeezable hand bulb 58 of the inflating apparatus 20 a one time purchase.

The inflating apparatus 20 further comprises a set of relief valves 60, with one relief valve of the set of relief valves 60 of the inflating apparatus 20 at a time being in fluid communication with the filler tube 52 of the inflating apparatus 20, between the squeezable hand bulb 58 of the inflating apparatus 20 and the one bladder of the pair of bladders 18, and which prevents over inflation of the pair of bladders 18 preventing unnecessary trauma.

The set of relief valves 60 of the inflating apparatus 20 are interchangeable which allows changes needed in head lifting pressure as clinical conditions warrant in the wearer 14 as need arises.

The cervical collar for lifting the skull of a wearer 10 further comprises a cover 62 that covers the collar 16 and the pair of bladders 18 as a unit, with the inflating apparatus 20 depending therethrough.

The cover 62 is washable absorbent cloth.

It will be understood that each of the elements described above, or two or more together, may also find a useful application in other types of constructions differing from the types described above.

While the invention has been illustrated and described as embodied in a cervical collar for lifting the skull, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A cervical collar for lifting the skull of a wearer, comprising:

a) a core for replaceably encircling the neck of the wearer and having a non-wearing position and a wearing position; said core having a pair of free ends overlapping for facing the back of the neck of the wearer when said core is in said wearing position, with said core being releasably maintained in said wearing position by mating portions of hook and loop fasteners disposed on adjoining faces of said pair of free ends of said core;

b) a pair of bladders being inflatable and disposed on said core; said core further having an inner surface with a pair of sides for facing the sides of the neck of the wearer, with each bladder of said pair of bladders only being disposed on a respective side of said pair of sides of said inner surface of said core; each bladder of said pair of bladders having an upper edge for facing the skull of the wearer; said upper edge of each bladder of said pair of bladders having:

i) a proximal end with a cushion thereon for contacting only a point behind a respective angle of the jaw of the wearer; and ii) a distal end with another cushion thereon for contacting the base of the skull of the wearer, only at a respective nuchal point on a respective side of the base of the skull of the wearer, with the point behind the respective angle of the jaw of the wearer and the respective nuchal point on the respective side of the base of the skull of the wearer being those portions of the skull of the wearer that are sufficient for handling upward supporting and lifting pressure when said pair of bladders are inflated; and c) inflating apparatus in fluid communication with said pair of bladders, and when said pair of bladders are inflated to a predetermined pressure by said inflating apparatus, the skull of the wearer is gently pushed off the shoulders of the wearer, which relieves downward pressure on the cervical spine of the wearer by forming intrinsic neck traction, whose early and continued use relieves pain and weakness and prevents major and sometimes non-reversible deterioration of the cervical spine of the wearer; said inflating apparatus comprising a filler tube depending at one end thereof from, and in fluid communication with, one bladder of said pair of bladders, and terminating at another end thereof; said inflating apparatus further comprising a squeezable hand bulb in fluid communication with said another end of said filler tube of said inflating apparatus, and when squeezed, inflating said pair of bladders; said inflating apparatus further comprising a set of relief valves, with one relief valve of said set of relief valves of said inflating apparatus at a time being in fluid communication with said filler tube of said inflating apparatus, between said squeezable hand bulb of said inflating apparatus and said one bladder of said pair of bladders, and which prevents over inflation of said pair of bladders preventing unnecessary trauma; said set of relief valves of said inflating apparatus being interchangeable which allows chances needed in head lifting pressure as clinical conditions warrant in the wearer as need arises.

2. The collar as defined in claim 1, wherein said core is washable foam and has a consistency in a range of soft to firm, depending upon needs of the wearer.

3. The collar as defined in claim 1, wherein said pair of bladders are manufactured from washable latex and flexible enough to allow for movement of the neck of the wearer in all directions, while allowing for movement of the jaw of the wearer for talking and eating without sacrificing any upwardly lifting pressure of said pair of bladders.

4. The collar as defined in claim 1, wherein said pair of bladders are in fluid communication with each other by a tube that extends along said inner surface of said collar, opposite to said pair of free ends of said core.

5. The collar as defined in claim 1, wherein said squeezable hand bulb of said inflating apparatus is interchangeably disposed on said another end of said filler tube of said inflating apparatus so as to be useable with successive said cervical collar for lifting said skull of a wearer which makes said squeezable hand bulb of said inflating apparatus a one time purchase.

6. The collar as defined in claim 1; further comprising a cover that covers said collar and said pair of bladders as a unit, with said inflating apparatus depending therethrough.

7. The collar as defined in claim 6, wherein said cover is washable absorbent cloth.

* * * * *